(12) United States Patent
Wagner et al.

(10) Patent No.: US 6,637,254 B2
(45) Date of Patent: Oct. 28, 2003

(54) SENSOR ELEMENT HAVING A PROTECTIVE DEVICE

(75) Inventors: Wolfgang Wagner, Korntal-Muenchingen (DE); Volker Gandert, Unterriexingen (DE)

(73) Assignee: Robert Bosch GmbH, Stuttgart (DE)

( * ) Notice: Subject to any disclaimer, the term of this patent is extended or adjusted under 35 U.S.C. 154(b) by 28 days.

(21) Appl. No.: 09/969,266

(22) Filed: Oct. 1, 2001

(65) Prior Publication Data

US 2002/0069698 A1 Jun. 13, 2002

(30) Foreign Application Priority Data

Sep. 29, 2000 (DE) .......................................... 100 48 241

(51) Int. Cl.$^7$ ............................................ G01N 27/403
(52) U.S. Cl. ...................... 73/31.05; 73/23.31; 204/428
(58) Field of Search ............................... 73/23.2, 23.31, 73/31.05; 204/428; 338/277

(56) References Cited

U.S. PATENT DOCUMENTS

| | | | | | |
|---|---|---|---|---|---|
| 4,065,372 | A | * | 12/1977 | Hacker et al. | ............... 204/428 |
| 4,199,424 | A | * | 4/1980 | Teitelbaum | .................. 204/428 |
| 4,507,192 | A | * | 3/1985 | Ebizawa et al. | ............. 204/428 |
| 4,624,770 | A | * | 11/1986 | Yamada et al. | ............. 204/428 |
| 4,756,885 | A | * | 7/1988 | Raff et al. | ................... 204/428 |
| 4,916,934 | A | * | 4/1990 | Nagata et al. | ............. 73/31.05 |
| 4,929,331 | A | * | 5/1990 | Kato et al. | .................. 204/428 |
| 5,012,670 | A | * | 5/1991 | Kato et al. | ................. 73/31.05 |
| 6,346,179 | B1 | * | 2/2002 | Makino et al. | ............. 204/428 |

* cited by examiner

Primary Examiner—Daniel S. Larkin
(74) Attorney, Agent, or Firm—Kenyon & Kenyon

(57) ABSTRACT

A sensor element is proposed, particularly a lambda probe for analyzing exhaust gases in internal combustion engines, having a protective device which, at least region-wise, surrounds or covers a sensitive component of the sensor element exposed to a gas. Also provided is that the protective device has an arrangement or is joined to such an arrangement by which the admission of gas to the sensitive component is able to be regulated.

11 Claims, 2 Drawing Sheets

SENSOR ELEMENT HAVING A PROTECTIVE DEVICE

FIELD OF THE INVENTION

The present invention relates to a sensor element, particularly a lambda probe for analyzing exhaust gases of internal combustion engines, having a protective device.

BACKGROUND INFORMATION

The sensitive component of customary lambda probes, as are often used for analyzing exhaust gases in the exhaust system of internal combustion engines, is usually surrounded by a protective sleeve to protect against damage as a result of mechanical and thermal influences; the protective sleeve allows the admission of the exhaust gas to be analyzed through suitable openings to the sensitive component of the lambda probe arranged within the protective sleeve. This protective sleeve is used first of all to avoid transport and installation damage, as well as to avoid thermal shock stress of the actual sensitive, heated lambda-probe component due to contact with drops of water.

Such a protective sleeve represents a compromise between sufficient protective action, especially against water admission during cold starts in the following warm-up phase of the engine, and the lowest possible reaction time of the measuring signal of the sensor element in response to a change in the oxygen content in the exhaust gas.

In order not to reduce the reaction time of the sensor element too much, e.g. by a design of the protective sleeve with very high protective action, under the state of the art the protective sleeve is designed such that in the warm-up phase of the engine, action of water or water drops on the sensitive component of the sensor element cannot initially be ruled out completely. At the same time, however, until the dew-point temperature of water in the applied exhaust gas is reached by increasing warm-up of the engine, the heating of the sensitive component to its optimal operating temperature is at first reduced through a change in the heating power to the extent that the temperature of the sensitive component, designed, for example, as a ceramic platelet, does not exceed a temperature of approximately 400° C. Only when the warm-up phase of the engine has terminated or has advanced so far that the temperature of the applied exhaust gas has exceeded the dew-point temperature of water is the heating power increased to the extent that the sensitive component reaches its operating temperature of approximately 750° C.

It may be that this procedure leads to a good reaction time of the lambda probe, however, it has the disadvantage that in the warm-up phase of the engine, because of the initially lowered operating temperature, the lambda probe is not yet ready for measurements, i.e. operates inadequately for a steady control.

In addition, in known methods heretofore, when the exhaust-gas temperature has exceeded the dew-point temperature of water, i.e. after successful warm-up of the engine, the protection of the sensitive component of the gas sensor implemented up to now by the protective sleeve is no longer necessary to the degree as during the warm-up phase of the engine. The protective sleeve then merely increases the time constants of the lambda probe in an unnecessary manner.

SUMMARY OF THE INVENTION

The object of the present invention was is to improve the reaction time of the sensor element in all operating states, accompanied at the same time by sufficient protective action, especially against water admission in the region of the sensitive component of the sensor element.

Compared to the related art, the sensor element of the present invention has the advantage that the admission of gas to the sensitive component is adapted to the specific operating parameters of the sensor element and in particular to the temperature of the applied gas, so that, for example, when used in a lambda probe, the protection of the actual sensitive component is improved by the protective device in the warm-up phase of an internal combustion engine, and when the engine is at operating temperature, the reaction time of the sensor element is reduced, leading to functional advantages in the engine management.

It is particularly advantageous that a software, used frequently till now, for modeling the time-dependent exhaust-gas temperature in the engine management or the heating may be omitted or markedly reduced with respect to its scope.

Thus, it is particularly advantageous if the admission of gas to the sensitive component is regulated as a function of temperature, so that the admittance of gas to the sensitive component is enabled or facilitated at or above a first temperature, while the gas admission is prevented or hindered at or below a second temperature which is lower compared to the first temperature.

It is also advantageous if the protective device is a customary protective sleeve or a protective cap provided with a bimetal region. This bimetal region is preferably a bimetal strip or a bimetal flap, inserted into the protective sleeve or the protective cap or joined to it, with which the size of the gas-admission openings in the protective device can be changed as a function of temperature, and consequently the admission of gas to the sensitive component can be regulated, In the same way, it is advantageous if the protective device has a bimetal bellows, a part of such a bellows or an expansion structure that is optionally joined to a supporting body and the protective device, and via which the admission of gas to the sensitive component is able to be regulated The gas-admission openings in the protective device, which are variable as a function of temperature, are advantageously designed so that the sensitive component of the sensor element is optimally protected against water admission at exhaust-gas temperatures below the dew point temperature of water, but at higher temperatures the most optimal exhaust-gas accessibility possible is provided. In this way, due to the optimal protection against water admission, the sensitive component can already be heated to the necessary operating temperature even before the dew point temperature of the applied gas has been reached, so that the functioning of the sensor element is continually fulfilled even at low temperatures, i.e. in the warm-up phase of the engine.

DETAILED DESCRIPTION

The exemplary embodiments explained below start out initially as sensor element 5, provided with a protective device, of a known planar lambda probe for analyzing exhaust gases in internal combustion engines, which is incorporated in a known manner in the exhaust-gas system of a motor vehicle.

Figure 1:
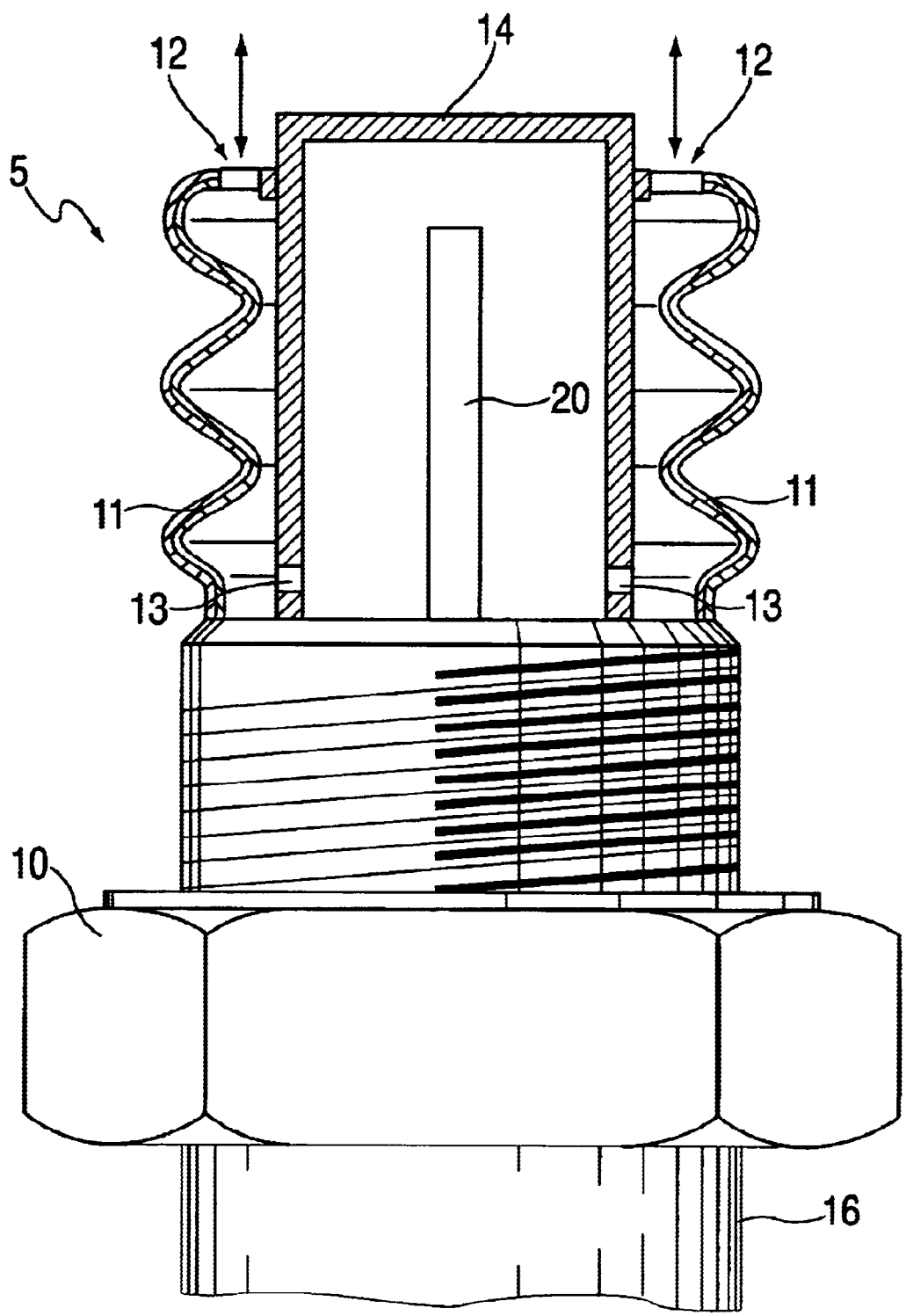
FIG. 1 shows a sensor element having a protective device and a bellows-type expansion structure.

To that end, according to FIG. 1, sensor element 5 has a nut 10 and a supporting body 16 with which sensor element 5 is mounted in the exhaust flow of the exhaust-gas system. FIG. 1 shows only the part of sensor element 5 which is situated above nut 10 and above supporting body 16, and which is located in the exhaust flow. Representation of the remaining parts of sensor element 5 with probe housing and electrical connections has been omitted.

FIG. 1 further shows that sensor element 5 has a sensitive component 20 which, in the specific case, is a generally known ceramic platelet of a planar lambda probe, and which is surrounded by a protective sleeve 14 that has first gas-admission openings 13 via which admission of the exhaust gas to sensitive component 20 is possible. The number of first gas-admission openings 13 and their arrangement can be adapted to the requirements of the specific individual case. For example, protective sleeve 14 is a metallic cap.

In the example explained, first gas-admission opening 13 is in the form of a slit, particularly a slit running around protective sleeve 14, so that protective sleeve 14 is supported in a floating manner by a retaining device explained below, and protective sleeve 14 surrounds sensitive component 20 with clearance. The retaining device supporting protective sleeve 14 is a bimetal bellows 11 in the form of a rippled bimetal sheet, so that on one hand it surrounds protective sleeve 14 concentrically, and on the other hand is joined both to supporting body 16 and to protective sleeve 14. In the example explained, bimetal bellows 11 is joined to protective sleeve 14 in the region of the end of protective sleeve 14 facing away from nut 10, where, for example, bimetal bellows 11 is welded to protective sleeve 14.

Furthermore, in the region of the connection between bimetal bellows 11 and protective sleeve 14, second gas-admission openings 12 are provided which, for example, are in the form of holes or short slits. They are used to admit the gas to be analyzed into the space between bimetal bellows 11 and protective sleeve 14, from where it can then enter further via first gas-admission openings 13 into the inside space of protective sleeve 14, and there be analyzed by sensitive component 20 with respect to the concentration of individual gas components, e.g. with respect to the oxygen content.

It is apparent that the design of bimetal bellows 11 according to FIG. 1 is subject to many different variants which, however, are similar in their function. Thus, for example, bimetal bellows 11 can also be designed as a bimetal bellows which does not completely run around protective sleeve 14, so that it supports protective sleeve 14 only region-wise. Furthermore, bimetal bellows 11 can also be constructed in other forms generally as an expansion structure which has the task of making first gas-admission openings 13 and/or second gas-admission openings 12 larger or smaller as a function of the specific temperature of the exhaust gas.

Due to bimetal bellows II or such an expansion structure, the admission of gas to sensitive component 20 is able to be regulated as a function of the temperature of this gas in such a way that at and/or above a first temperature, the admittance of gas to sensitive component 20 is permitted or facilitated, while at and/or below a second temperature which is lower compared to the first temperature, the admittance of gas to the sensitive component is prevented or hindered. In this context, it can also be provided in particular that first gas-admission openings 13 and/or second gas-admission openings 12 are completely closed below a certain limiting temperature.

A continual change in the size of first gas-admission openings 13 and/or of second gas-admission openings 12, and thus of the gas admission to sensitive component 20 is preferably implemented by way of bimetal bellows 11, i.e. the expansion structure. Achieved all in all by the temperature-dependent change in the admittance of gas through gas-admission openings 12, 13 to sensitive component 20 explained, is that at low exhaust-gas temperatures, which are to be allocated to a cold start or a warm-up phase of the internal combustion engine, sensitive component 20 which is usually heated to temperatures above 400° C. is protected from the entrance of water drops or other impurities contained in the exhaust gas at this point of time.

Incidentally, one variant of the exemplary embodiment according to FIG. 1 provides for a stop arrangement in the region of first gas-admission openings 13, so that even at low exhaust-gas temperatures, sensitive component 20 is always in contact with the gas to be analyzed outside of protective sleeve 14 through a defined minimal size of gas-admission openings 13.

Figure 2:
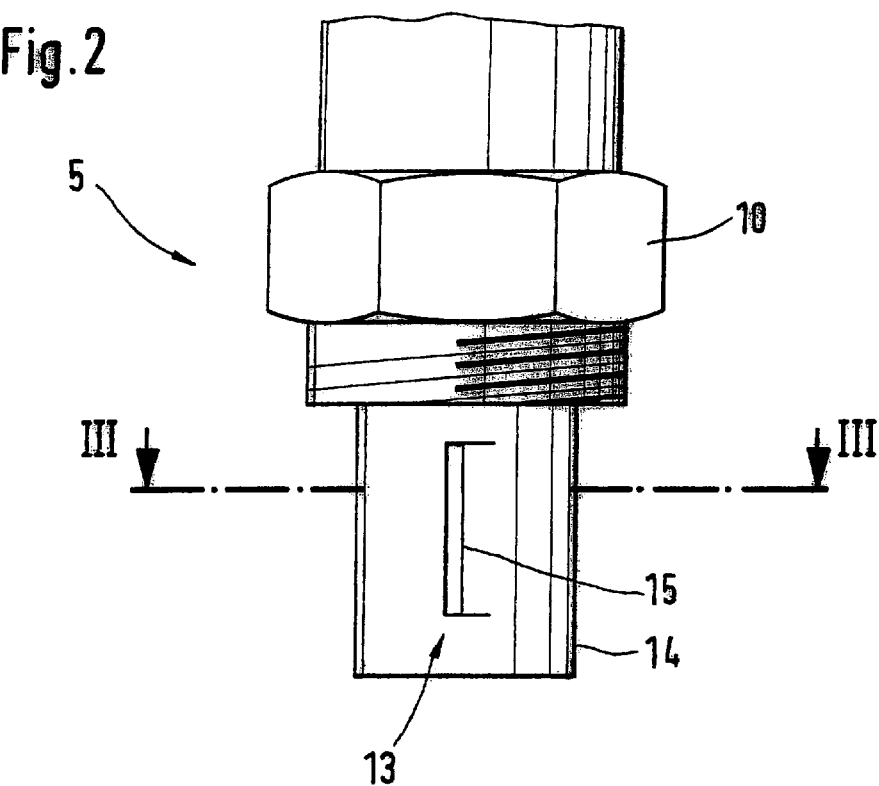
FIG. 2 shows a second exemplary embodiment of the sensor element having a protective device and a bimetal strip inserted into it.

FIG. 2 clarifies a second exemplary embodiment of a sensor element 5 with protective device, in which, deviating from the exemplary embodiment according to FIG. 1, it is possible to dispense with bimetal bellows 11 by first of all providing a customary protective sleeve 14 made, for example, of metal, which has at least one, e.g. slit-shaped first gas-admission opening 13. In addition, however, in this protective sleeve 14 according to FIG. 2, in the region of the gas-admission openings a bimetal region, joined to protective sleeve 14, is in each case preferably employed in the form of a bimetal strip 15 or a bimetal flap made of a bimetal strip or a bimetal sheet designed in a known manner.

Figure 3:
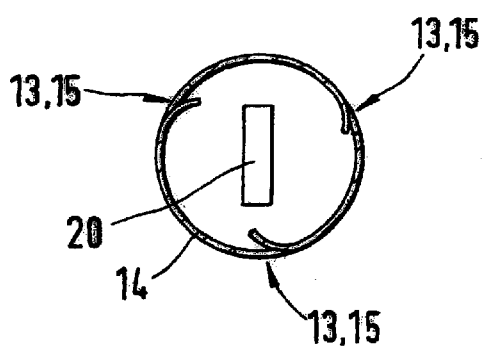
FIG. 3 shows a section through FIG. 2 along intersection line 111—111

To that end, FIG. 3 shows that, analogous to FIG. 1, sensitive component 20 is situated in the center of protective sleeve 14 and is surrounded by a plurality of slit-shaped gas-admission openings 13 which in each case are joined with a bimetal flap or a bimetal strip 15 in such a way that the gas passage is alterable by varying the size of gas-admission openings 13 with the aid of bimetal strips 15 as a function of the temperature. In particular, at low temperatures, first gas-admission openings 13 are completely or substantially closed by bimetal strips 15, or the admission of gas through gas-admission openings 13 is reduced to a minimum, while at higher temperatures, bimetal flaps or strips 15 bend and enlarge first gas-admission openings 13 so as to facilitate the admission of gas to sensitive component 20.

Figure 4:
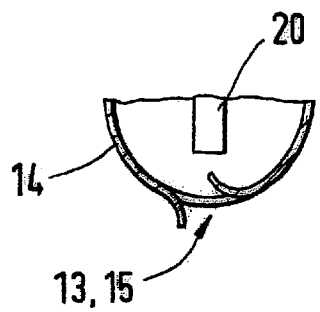
FIG. 4 shows an alternative exemplary embodiment to FIG. 3.

The practical design of bimetal strips or bimetal flaps 15 according to FIGS. 2 and 3, respectively, is subject to diverse variations, which is clarified with the aid of FIG. 4. There, two bimetal strips 15, allocated to a shared gas-admission opening 13, are arranged opposite one another.

What is claimed is:

1. A sensor element, comprising:
   a protective device that one of surrounds and covers a sensitive component of the sensor element exposed to a gas; and
   an arrangement that is one of included in the protective device and joined to the protective device and by which an admission of the gas to the sensitive component is able to be regulated.

2. The sensor element according to claim 1, wherein:

the gas corresponds to an exhaust gas, and the sensor element corresponds to a lambda probe for analyzing the exhaust gas in an internal combustion engine.

3. The sensor element according to claim 1, wherein:

the admission of the gas is able to be regulated as a function of a temperature of the gas in such a way that at a temperature that is equal to at least a first temperature, the admission of the gas to the sensitive component is one of permitted and facilitated so that the gas is at least partially admitted, and at another temperature that is no more than a second temperature that is lower than the first temperature, the admission of the gas to the sensitive component is one of prevented and hindered.

4. The sensor element according to claim 1, wherein:

the protective device includes one of a protective sleeve and a protective cap.

5. The sensor element according to claim 1, wherein:

the protective device is constructed in such a way that one of drops of water, dirt particles, and impurities of the gas do not gain admittance to the sensitive component.

6. The sensor element according to claim 1, wherein:

the protective device includes at least one first gas-admission opening.

7. The sensor element according to claim 1, wherein:

the arrangement includes at least one bimetal region joined to the protective device.

8. The sensor element according to claim 7, wherein:

the protective device includes a protective sleeve, the protective device includes at least one first gas-admission opening, and the at least one bimetal region includes one of a bimetal strip and a bimetal flap that is one of inserted into and joined to the protective sleeve, with which a size of the at least one first gas-admission opening is variable as a function of a temperature.

9. The sensor element according to claim 1, further comprising:

a supporting body, wherein:

the arrangement includes one of a bimetal bellows, a part of the bimetal bellows, and an expansion structure that is joined to the supporting body and the protective device, and by which the admission of the gas to the sensitive component is able to be regulated.

10. The sensor element according to claim 9, wherein:

the protective device includes at least one first gas-admission opening, and a size of the at least one first gas-admission opening is alterable by one of the bimetal bellows, the part of the bimetal bellows, a bimetal region, a bimetal strip, a bimetal flap, and the expansion structure as a function of a temperature.

11. The sensor element according to claim 1, wherein:

the sensitive component is arranged in an exhaust flow of an internal combustion engine.

* * * * *